United States Patent [19]

Sakariassen

[11] Patent Number: 5,662,107
[45] Date of Patent: Sep. 2, 1997

[54] DEVICE AND A METHOD FOR MEASURING THROMBUS FORMATION TENDENCY

[75] Inventor: Kjell Steinar Sakariassen, Oslo, Norway

[73] Assignee: Nycomed Imaging AS, Oslo, Norway

[21] Appl. No.: 464,659

[22] PCT Filed: Dec. 29, 1993

[86] PCT No.: PCT/NO93/00199

§ 371 Date: Jun. 15, 1995

§ 102(e) Date: Jun. 15, 1995

[87] PCT Pub. No.: WO94/16326

PCT Pub. Date: Jul. 21, 1994

[30] Foreign Application Priority Data

Dec. 30, 1992 [NO] Norway .................................. 925047

[51] Int. Cl.$^6$ ................................................ A61B 5/00
[52] U.S. Cl. ........................ 128/637; 128/632; 128/760; 128/692
[58] Field of Search ...................... 128/760, 63, 768, 128/72, 692, 637, 638, 771, 632; 436/69, 66

[56] References Cited

U.S. PATENT DOCUMENTS

| 4,780,418 | 10/1988 | Kratzer | 128/673 X |
| 5,275,953 | 1/1994 | Bull | 128/770 X |

FOREIGN PATENT DOCUMENTS

| 88/02116 | 3/1988 | WIPO . |
| 91/02976 | 3/1991 | WIPO . |
| 93/00989 | 1/1993 | WIPO . |

OTHER PUBLICATIONS

*Arterioscleriosis*, vol. 10, No. 2, 1990 by Kjell S. Sakariassen et al. "Collagen Type III Induced Ex Vivo Thrombogenesis in Humans".

Primary Examiner—Lee S. Cohen
Assistant Examiner—Ryan Carter
Attorney, Agent, or Firm—Birch, Stewart, Kolasch & Birch

[57] ABSTRACT

A device for in vitro measurement of a tendency to form thrombi in people and animals under simulated in vivo conditions. Blood is pumped at a constant flow through at least one flow channel. This flow channel can be coated or made of a thrombogenesis-promoting material. The pressure difference between the pressures upstream and downstream of the thrombogenesis unit, due to a thrombus formed in the flow channel, is measured. With this device, a method can measure the tendency to thrombogenesis.

21 Claims, 3 Drawing Sheets

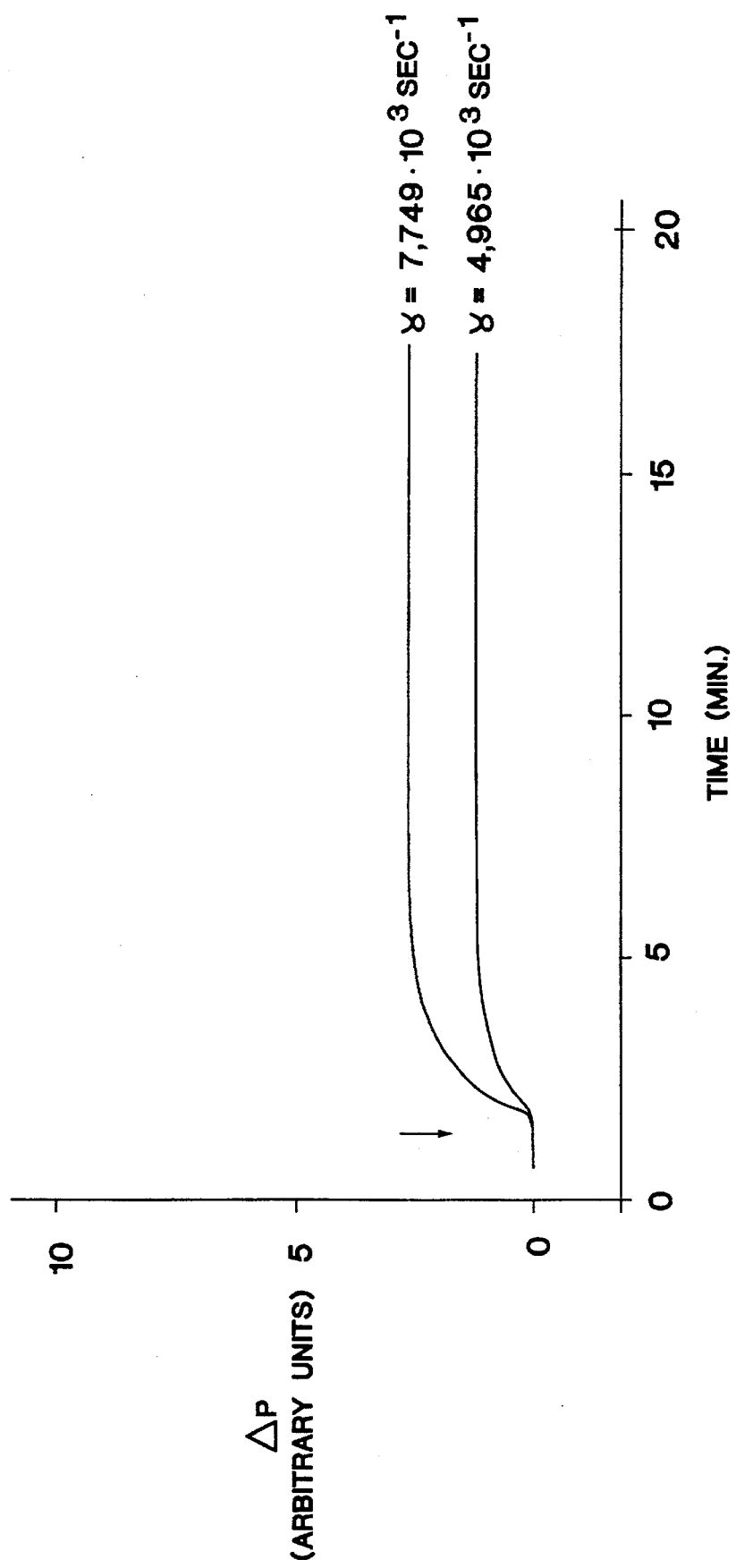

DEVICE AND A METHOD FOR MEASURING THROMBUS FORMATION TENDENCY

FIELD OF THE INVENTION

The invention concerns a device and a method for measuring the tendency to form blood clots in vitro by using non-anticoagulated venous blood which is pumped through one or more parallel synthetic channels with different diameters, "thrombogenesis units", which simulate in vivo bloodstream conditions, and where the fluid pressure is recorded before and after the thrombogenesis units, and the pressure drop is calculated as a function of the flow time, which will be an expression of how quickly a thrombosis is formed in the system.

DESCRIPTION OF THE PRIOR ART

The blood contains red and white blood corpuscles, plasma proteins and blood platelets and circulates in a closed circuit where the heart supplies the energy which impels the blood through the arterial part of the circuit. The consequences of clogging of this circuit vary in severity, depending on whether the peripheral circulation, cardial, pulmonary or cerebral circulation is affected. A considerable number of people in the industrialized part of the world are disabled or die due to circulatory disturbances and it is therefore vital from the social and economic points of view to be able to detect as early as possible the onset of possible circulatory problems, e.g. a thrombogenetic tendency, under different conditions and to monitor antithrombotic treatment.

To transport blood through a blood vessel, from a point A to a point B, the pressure in A ($P_A$) must be greater than the pressure in B ($P_B$). The blood flow from A to B, Q, is dependent on $P_A-P_B$ and the resistance R to the flow, according to formula I;

$$Q = \frac{P_A P_B}{R} = \frac{\Delta P}{R} \quad \text{(I)}$$

In an undamaged blood vessel the blood flow will be laminar and in accordance with Poiseuille's law, expressed in formula II;

$$Q = \frac{\pi \Delta P r^4}{8 \eta l} \quad \text{(II)}$$

where r=radius of the vessel
l=length of the vessel
η=viscosity of the blood.

It can be seen in formulae I and II that the resistance can thereby be expressed by III;

$$R = \frac{8}{\pi} \cdot \eta \cdot \frac{l}{r^4} \quad \text{(III)}$$

This shows that the resistance to the flow is affected by characteristics of the blood vessel (length and radius) together with the viscosity of the blood. In a vessel the flow profile will describe a parabolic shape, the layers which are closest to the wall of the vessel will adhere to the wall, while towards the middle of the stream the liquid layers will slide towards one another and the viscosity alone affects the flow picture. Thus the shear rate will be highest at the wall (see below).

With an increase in the speed of the blood the flow will remain laminar, and thus comply with Poiseuille's law, until a critical speed is reached, above which the flow becomes turbulent. In this state Osborne Reynolds demonstrated that the energy which drives the fluid is mainly used to create kinetic energy and the resistance to the flow will now depend on the density of the fluid instead of its viscosity, as was the case when the flow was laminar. The combination of turbulence and reduced vessel diameter will increase the resistance and lead to an increased drop in pressure over a vessel area in which there is a constriction.

Thrombosis can arise as a result of activation of blood platelets with a resultant aggregation of these and/or coagulation of blood which includes blood platelet activation, the formation of prothrombin activator which in turn catalyzes the formation of thrombin from prothrombin.

This thrombin thereafter catalyzes the conversion of fibrinogen into filaments of fibrin, which form a network and entrap blood platelets, blood cells and plasma thus forming a coagulum. Coagulation and blood platelet deposits are initiated amongst other things by damage to the vascular surface, collagen fibres in the vessel wall and damaged endothelial cells. The formation of thrombi, which is partly responsible for circulatory disturbances, often with disabling or fatal results, can be activated by an uneven endothelial surface, as in the case of arteriosclerosis, infections or trauma. Similarly, a very slow blood flow can be subject to coagulation since small amounts of thrombin and other procoagulants are constantly being formed. The thrombi, which are rich in blood platelets on the arterial side and rich in fibrin filaments and red blood corpuscles on the venous side, are most frequently formed on the vessel wall where they reduce the vessel's diameter. They can also be torn loose and carried with the blood to vital organs such as the lungs or brain, and form embolisms, with fatal results.

On the other hand, if the tendency to coagulation is reduced and in many cases if the formation of thrombi is reduced, a person will be subject to numerous small haemorrhages which can cause anaemia or, in serious cases, fatal haemorrhages.

Experiment had shown that many substances affect the formation of thrombi or thrombogenesis in flowing blood. These include synthetic polymers, such as, e.g., Dacron, biological materials, such as collagen fibrils, fibrin and other procoagulant protein-rich material (Baumgartner, H. R. Microvasc. Res. 5: 167, 1973; Baumgartner, H. R., Thromb. Haemostas. 37: 1, 1977; Sakariassen, K. S., Aarts, P. A. M. M., de Groot, P. G., Houdijk, W. P. M., Sixma, J. J. J. Lab. Clin. Med., 102: 522, 1983. It is further demonstrated that it is not so much the rate of the flowing blood as the shear rate at the blood vessel wall or flow channel wall which is important for the deposits of blood platelets and activation of coagulation (Sakariassen, K. S., Joss, R., Muggli, R., Kuhn, H., Tschopp, T. B., Sage, H., Baumgartner, H. R. Arteriosclerosis, 10: 276–284, 1990; Sakariassen, K. S., Weiss, H., Baumgartner, H. R. Thromb. Haemostas, 65: 596–600, 1991). Shear rates (γ) in round channels are expressed by formula IV;

$$\gamma \text{ wall} = 4 \frac{Q}{\pi r^3} \quad \text{(IV)}$$

where

Q=blood flow in ml/sec
r=radius in cm.

In flow channels with a rectangular cross section the shear rate (γ) at the wall is expressed by formula V;

$$\gamma(\text{wall}) = 1.03 \frac{Q}{a \cdot b^2} \quad \text{(V)}$$

where

Q=as above a=width of flow channel in cm b=height of flow channel in cm.

There are several known types of perfusion chambers, used to study characteristic features of thrombi formed in flowing blood, where the shear rate can be varied and a procoagulating surface can be introduced into the flow (Baumgartner, H. R. Thromb. Haemostas. 37: 1, 1977; Sakariassen, K. S., Aarts, P. A. M. M., de Groot, P. G., Houdijk, W. P. M., Sixma, J. J. J. Lab. Clin. Med. 102: 522, 1983). In Norwegian patent application no. 92 2247 and international application no. PCT/N092/00117 there is described a perfusion cheer where the flow channel cross section is constricted in order to simulate arteriosclerotic blood vessels and where the thrombi formed can be removed for closer inspection. These perfusion cheers are designed for studying the characteristic features in thrombogenic processes under simulated in vivo conditions, but they are not designed for mass study of the blood's tendency to form intravascular coagula or thrombi as a function of time.

SUMMARY OF THE INVENTION

To enable them to measure this, specialists use tests of bleeding time, by making an incision in, e.g., the ear or finger, coagulation time, where the time for coagulation is measured in a test tube which is shaken, and prothrombin time, where prothrombin is activated in a test tube and the time for coagulation is measured. There are, however, no specific tests for measuring the blood's tendency to form clots under standardised, reproducible circulatory conditions, which simulate the conditions in normal and pathological blood vessels, since the above-mentioned tests are based on a blood sample which is treated in a test tube. All known tests measure individual mechanisms in the complicated thrombogenesis. Thus, it is an object of the present invention to provide a device and method for measuring the total response in flowing blood. It is a further object to use native blood which has not been anti-coagulated.

These objects are achieved by the present invention characterized by the claims presented.

The present invention comprises an infusion set with a "Butterfly needle" where the needle is inserted into a suitable vein, e.g. a person's arm vein, and is connected via a mixing device, described in Norwegian patent application 92 2247 and PCT/N092/00117, or via an adaptor, with one or more parallel channel systems where at least the Walls consist of, or are internally coated with material which can activate or promote thrombogenesis. These materials may inclulde polymers, such as polyester, e.g. Dacron, polytetrafluorethylene (PTFE, Teflon) and Thermanox® plastic, and vessel wall components which promote thrombosis, e.g. collagen, fibronectin, von Willebrand factor, tissue factor and phospholipids or other thrombosis-promoting molecules. The channels have dimensions which give shear rates typical for arteries, veins and sclerotic arteries (formula IV), where the fluid pressure is measured by means of known per se methods upstream and downstream of the thrombogenesis unit or units, and where the blood is sucked through the thrombogenesis unit or units by means of a suction pump. The formation of clots or thrombi in the channel systems will alter the vessel dimensions and thereby affect the pressure drop over the thrombogenesis unit or units, the resistance to the flow being altered when the flow is kept constant (formulae I, II, III).

The tendency to blood clot formation is measured as the change in the pressure drop ($\Delta P$) as a function of the flow time.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be explained in more detail by describing preferred designs, drawings which are given by way of illustration only, and thus are not limitative of the present invention, and wherein:

FIG. 4 shows pressure differences (arbitrary units) measured as a function of time (min.) when citrate blood is pumped through a thrombogenesis unit according to the invention, with Dacron in the flow channel's walls, with two different shear rates at the wall with the arrow indicating the start of flow.

DESCRIPTION OF THE PREFERRED EMBODIMENT

Figure 1:
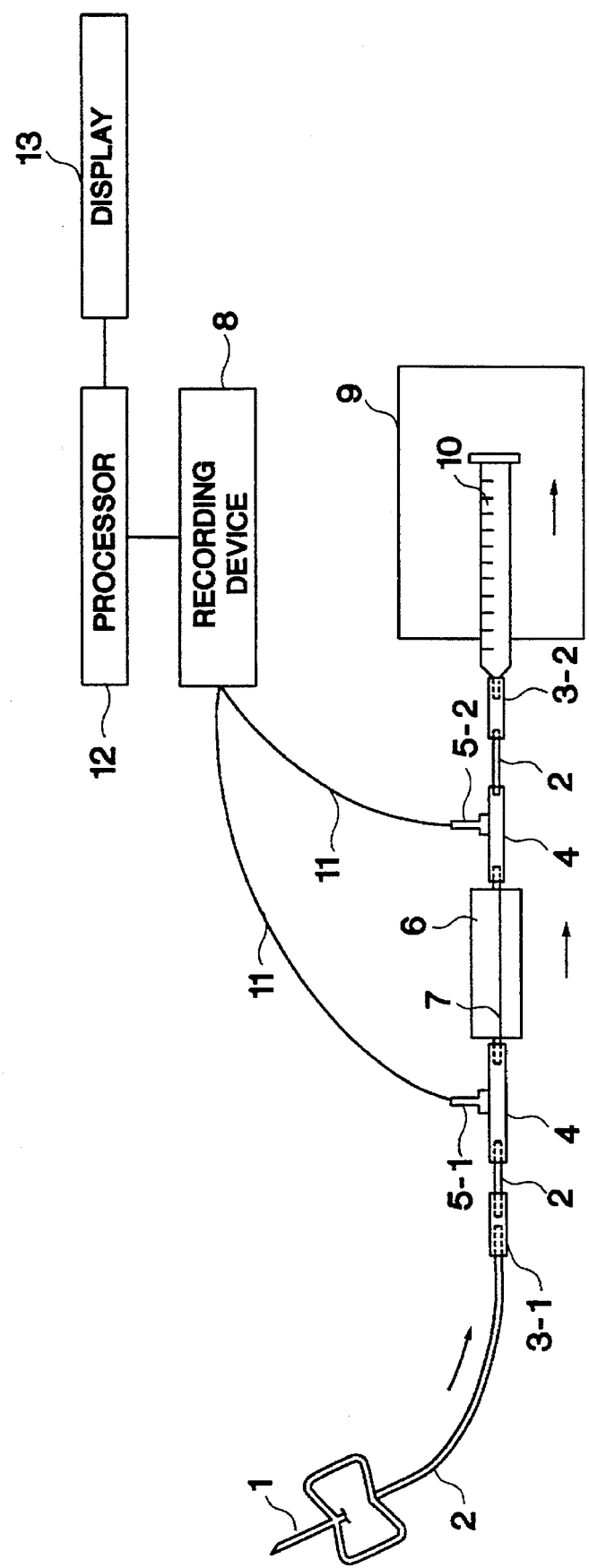
FIG. 1 is a schematic illustration of a simple design of the device according to the invention, with one thrombogenesis unit.

A simple design of the device according to the invention, with one thrombogenesis unit, is illustrated in FIG. 1. More complicated designs are developed by combining this simple design in such a way that the system comprises several parallel-connected thrombogenesis units, with related pump devices and pressure sensors. The needle 1 in an infusion set, e.g. of the "Butterfly" type, is inserted into a suitable vein, e.g. a person's arm vein. The needle 1 is successively connected to different members beginning with suitable tubes 2 and then an adaptor 3-1. A T-tube 4 with presure sensor 5-1 is next in line. The pressure sensor 5-1 measures the fluid pressure before the thrombogenesis unit, e.g. thrombosis chamber 6. This chamber 6 has a through-flow 7. A T-tube 4 with pressure sensor 5-2 for measuring the fluid pressure after the thrombogenesis unit 6 is connected to the downstream side of unit 6. An adaptor 3-2 for the syringe 10 is then provided. The syringe 10 is in a device 9 which pulls the syringe out, such as a Harvard pump. The pressure sensors 5-1, 5-2 are electrically connected 11 with a suitable recording device 8, with an electronic device 12 for calculation and storage of the result sin the form of a pressure drop as a function of flow time, and a device 13 for displaying the results, such as an electronic screen device and/or paper printer device.

The thrombosis chamber 6 can be in the form of a block, e.g. 2 cm long and 1.2 cm wide and 1 cm thick, made of a synthetic material which activates/promotes thrombogenesis, such as polyester fibre, e.g. Dacron, or other suitable materials. In the longitudinal direction of the block there are drilled out one or more flow channels with a circular cross section and with a radius calculated according to which shear rates are desirable at the wall in the blood flow concerned. When using formula IV, for example, suitable shear rates will be calculated for a specific blood flow and the radius of the flow channel. When venous conditions are simulated, suitable shear rates are $\leq 100$ sec$^{-1}$, preferably 20–100 sec$^{-1}$, specially preferred 40–60 sec$^{-1}$. Under arterial conditions the shear rate is between 100 and 1500 sec$^{-1}$, preferably between 300 and 1000 sec$^{-1}$, specially preferred 400–800 sec$^{-1}$. The shear rate in sclerotic arteries is $\geq 1500$ sec$^{-1}$, preferably 1500–40 000 sec$^{-1}$, specially preferred 4000–8000 sec$^{-1}$. The flow can vary between 0.1 and 10 ml/min.

The thrombogenesis unit can also be in the form of a tube, with internal radii adapted to the flow in order to obtain the desired shear rates, made of a material which activates/promotes thrombogenesis, or where the length of the tube is adapted to give adequate sensitivity for recording a pressure drop over the thrombosis tube.

A further design of the thrombogenesis unit comprises a perfusion device with a measuring chamber device according to Norwegian patent application no. 92 2247 and international patent application PCT/N092/00117, where the flow channel, which is drilled longitudinally through a hard plastic block, conveys the blood into a measuring chamber with a rectangular flow cross section, where the top/bottom is composed of a measuring chamber device. This top/bottom is inserted into the flow channel by means of a profile in the direction of flow, thus creating a unilateral constriction of the flow cross section, and in suitable grooves before, on and after the insertion there are fitted cover plates, uncoated or coated with biological material or chemical compounds which are suitable for activation of thrombogenesis. The bottom/top of this measuring chamber, opposite the bottom of the measuring chamber device, can also be inserted into the flow channel in order to create a bilateral constriction. The advantage of using this device is that the cover plate can be coated with any desired material, including native biological material from the person undergoing the measurement, and the thrombus created on the cover plate may be removed by removing the cover glass and subjected to closer inspection.

According to a design of the device according to the present invention, adaptor 3-1 (FIG. 1) can be replaced by a mixing device as described in Norwegian patent application no. 92 2247 and international patent application PCT/N092/00117, when the effect on the tendency to blood clotting of added solutions requires to be studied. This mixing apparatus comprises a modified T-tube in which solutions, such as, e.g., thrombogenesis modifying medication, may be added through the side tube, while the flow channel is tapered slowly after the side tube to approximately half the initial diameter, and then abruptly expanded over a substantially shorter length to a diameter considerably larger than the flow channel's initial diameter, in order thereby create turbulent flow and thus cause the solution, added through the side tube, to be homogeneously mixed with the bloodstream.

After a suitable needle has been inserted into a vein in a person or animal and connected to the device according to the invention for measuring the tendency to blood clotting, the pump 9, 10 is started up, which draws the venous blood from the vein, e.g. a person's arm vein, possibly through the mixing device or adaptor 3-1 and on through the T-tubes which contain the pressure sensors 5-1, 5-2 and the thrombogenesis unit's flow channel 7, with a flow which together with the diameter of the flow channel 7 gives the desired shear rate at the wall. Thrombosis or blood clots which occur in the flow channel 7 in the thrombosis chamber 6 constrict the flow channel cross section, increase the resistance (R) and thereby increase the pressure drop ($\Delta P$) from sensor 5-1 to sensor 5-2, according to formula I. Consequently sensor 5-2 will record lower fluid pressure than sensor 5-1, the signals from the pressure sensors are transmitted to the recording device 8, the pressure drop as a function of flow time is calculated by the electronic data processor 12 and stored, and the result is presented on a display device 13, such as an electronic screen device and/or a paper printer device.

The entire measuring procedure can use under 20 ml, preferably 5–10 ml of blood, and the measuring can last for less than 15 minutes, preferably 5–10 minutes.

Figure 2:
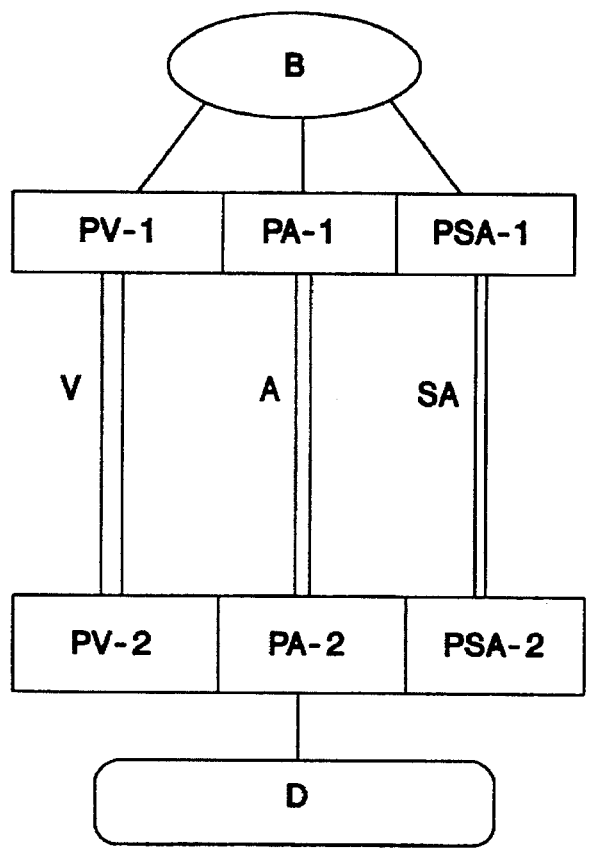
FIG. 2 is a principle view of a design with three parallel thrombogenesis units for simulation of circulation conditions in a vein (V), an artery (A) and a sclerotic artery (SA)

The concept of the invention comprises in vitro measuring of the tendency to form thrombosis under conditions which simulate in vivo circulatory conditions. A more complicated design comprises several parallel-connected systems with two or more thrombogenesis units, e.g. three, as illustrated in FIG. 2. There the blood's tendency to thrombogenesis as a function of flow time can be measured at the same time under conditions which simulate arterial (A), venous (V) and sclerotic arterial (SA) conditions. This is achieved by the use of three parallel thrombogenesis units, such as thrombosis chambers with one or more flow channels, thrombosis tubes and/or perfusion devices with measuring chamber devices, connected in parallel by replacing adaptor 3-1 with a branch unit. Each thrombogenesis unit is equipped with upstream and downstream pressure sensors (PV-1 and 2, PA-1 and 2, PSA-1 and 2) and a multichannel, e.g. 3-channel recording device with corresponding multichannel electronic data processor and storage device, and display of all the results on an electronic computer screen and/or by means of a paper printer device. The blood is drawn through the entire parallel-connected system by means of, e.g. the insertion of three volume-divided syringes in the pump device, which thereby suck blood through the system with the same flow. This design will save time and blood volume, the blood being removed by a single needle inserted into a suitable vein.

Figure 3:
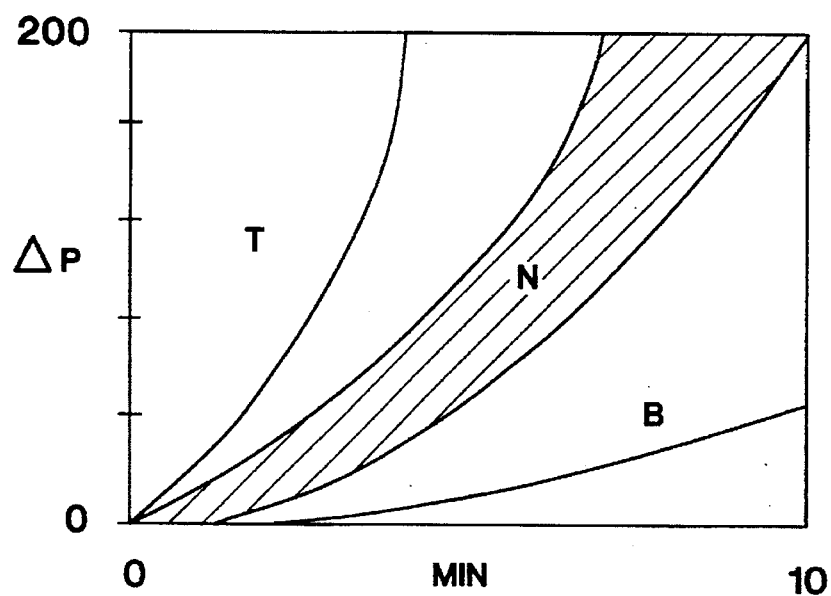
FIG. 3 illustrates how the pressure differences over the thrombosis unit ($\Delta P$) increase with perfusion time in a normal population (N), a population where the blood has an increased tendency to form clots (T) and a population where the blood has a reduced tendency to form clots, or an increased tendency to bleeding (B)

FIG. 3 illustrates the results from a possible mass study of the tendency to form thrombosis as a function of flow time with standardised shear rates in blood from healthy people (N), people with an increased bleeding tendency (B) and from people with an increased tendency to form thrombosis (T). This kind of figure is called a nomogram and is used in evaluating individual measurements performed by the method according to the invention and use of the device according to the invention.

The invention will now be illustrated more clearly by means of an embodiment example.

EXAMPLE

Venous blood was removed from the arm vein of a healthy person and anticoagulated with Na$_3$-citrate. The blood was then drawn through a thrombogenesis unit in which the walls of the flow channel were made of Dacron. The start of the perfusion is illustrated by an arrow in FIG. 4. The flow was 1 ml/min. and 0.64 ml/min., and the radius of the flow channel was 0.14 mm and the length approximately 2 cm. Thus, the shear rate at the wall was (formula IV) $\gamma=4.965.10^3$ sec$^{-1}$ when the flow was 0.64 ml/min. and $\gamma=7.749 \cdot 10^3$ sec$^{-1}$ with a flow of 1 ml/min. This corresponds to shear rates in sclerotic arteries.

As illustrated in FIG. 4 the pressure difference (ΔP) increased over the thrombogenesis unit to a constant value in the course of approximately the first 5 minutes of the perfusion. This increase in pressure difference shows that a thrombus has been formed in the thrombogenesis unit's flow channel. After a state of equilibrium has been achieved, FIG. 4 further illustrates that the drop in pressure increases with the shear rate and indicates that a greater part of the flow channel is occluded at higher shear rates.

The device was connected as shown in FIG. 1, with the exception that the "Butterfly" needle was removed as venous blood was removed from the vein in advance and anticoagulated.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

I claim:

1. A device for in vitro measurement of the tendency to form blood clots under conditions which simulate in vivo circulation conditions, the device comprising:

at least one tube of an infusion set for receiving fluid;

at least one upstream T-tube operatively connected to the at least one tube of the infusion set, the at least one upstream T-tube having at least one pressure sensor connected thereto;

at least one thrombogenesis unit connected to the at least one upstream T-Tube, the thrombogenesis unit including a thrombosis chamber with at least one flow channel, the thrombogenesis unit further having at least one of thrombosis tubes and perfusion chambers with measuring chamber devices having cover plates, the cover plates being one of coated and uncoated, at least one of the channel and thrombosis tubes being internally coated with materials which activate thrombogenesis, the at least one flow channel having a known shear rate for fluid flowing therethrough;

at least one downstream T-tube being connected to the at least one thrombogenesis unit, the downstream T-tube having at least one pressure sensor connected thereto;

a pump device connected to the downstream T-tube, the pump device having means for sucking fluid through at least one of the flow channels;

the pressure sensor for the upstream T-tube measures pressures upstream of the thrombogenesis unit and the pressure sensor for the downstream T-tube measures pressures downstream of the thrombogenesis unit;

means for recording a total volume of fluid pumped by the pump device, the means for recording being electrically connected to the pressure sensors for the upstream and downstream T-tube, the means for recording further recording upstream pressures and recording downstream pressures measured by the pressure sensors; and a data processing device connected to the means for recording, the data processing device calculates and stores changes in pressure drop between an upstream and downstream side of the thrombogenesis unit per time unit.

2. The device according to claim 1, further comprising one of an adaptor and branch pipe connected between the at least one tube of the infusion set and the upstream T-tube.

3. The device according to claim 1, further comprising means for displaying data received and stored in the data processing device.

4. The device according to claim 1, further comprising at least one mixing device attached to the device upstream of the thrombogenesis unit, the mixing device having inlet end pieces for adding solutions to fluid within the device.

5. The device according to claim 4, wherein the materials internally of at least one of the flow channel and thrombosis tubes are one of synthetic and biological and will activate thrombogenesis, the material being either coated on the at least one of the flow channel and thrombosis tubes or the at least one of the flow channel and thrombosis tubes being made from the material.

6. The device according to claim 1, wherein the at least one flow channel has a diameter such that a shear rate at a wall thereof is the proximate to in vivo arteries and wherein the rate is between 100 and 1500 sec$^{-1}$ for a flow of between 0.1 and 10 ml./min.

7. The device according to claim 6, wherein the rate is between 300 and 1000 sec$^{-1}$ for a flow of between 0.1 and 10 ml./min.

8. The device according to claim 1, wherein the at least one flow channel has a diameter such that a shear rate at a wall thereof is proximate to in vivo veins and wherein the rate is less than 100 sec$^{-1}$ for a flow of between 0.1 and 10 ml./min.

9. The device according to claim 8, wherein the rate is between 20 and 100 sec$^{-1}$ for a flow of between 0.1 and 10 ml./min.

10. The device according to claim 1, wherein the at least one flow channel has a diameter such that a shear rate at a wall thereof is proximate to in sclerotic arteries and wherein the rate is greater than 1500 sec$^{-1}$ for a flow of between 0.1 and 10 ml./min.

11. The device according to claim 10, wherein the rate is between 1500 and 40,000 sec$^{-1}$ for a flow of between 0.1 and 10 ml./min.

12. The device according to claim 1, wherein the at least one flow channel has a diameter such that an arterial shear rate at a wall thereof is between 400 and 800 sec$^{-1}$, a venous shear rate at the wall thereof is between 40 and 60 sec$^{-1}$, and an sclerotic arterial shear rate at the wall thereof is 4000 and 8000 sec$^{-1}$ for a flow of between 0.1 and 10 ml/min.

13. The device according to claim 1, wherein walls of the at least one of the flow channel and thrombosis tube are made of polyester fiber.

14. The device according to claim 1, wherein the cover plates are coated with materials which promote formation of thrombi.

15. The device according to claim 1, wherein the at least one thrombogenesis unit comprises two units with each being operatively connected to the at least one tube of the infusion set and operatively connected to the pump device and wherein each of the thrombogenesis units has at least one of flow channels, thrombosis tubes and perfusion chambers with a measuring chamber device, the two thrombogenesis units being connected in parallel and the device further comprising a branch pipe between the at least one tube of the infusion set and the two thrombogenesis units, an upstream pressure sensor and a downstream pressure sensor being provided for each thrombogenesis unit and the pressure sensors being operatively connected to the means for recording.

16. The device according to claim 15, wherein the pump device can selectively pump fluid through the two thrombogenesis units.

17. The device according to claim 1, wherein the at least one thrombogenesis unit comprises three units with each being operatively connected to the at least one tube of the infusion set and operatively connected to the pump device, each thrombogenesis unit having a flow channel which has a diameter such that during flow of fluid therethrough, an arterial shear rate at a wall thereof is between 100 and 1500 $\sec^{-1}$, a venous shear rate at the wall thereof is less than 100 $\sec^{-1}$, and an sclerotic arterial shear rate at the wall thereof greater than 1500 $\sec^{-1}$.

18. The device according to claim 17, wherein the arterial shear rate is between 400 and 800 $\sec^{-1}$, the venous shear rate is between 40 and 60 $\sec^{-1}$, and the sclerotic arterial shear rate is between 4000 and 8000 $\sec^{-1}$.

19. A method for measuring the tendency to form blood clots in an in vitro system which simulates in vivo circulation conditions, comprising the steps of:

inserting a tube into a vein of a human or animal;

drawing fluid from the vein with a suction pump;

measuring volume of the drawn fluid;

sucking the fluid through an upstream T-tube, the upstream T-tube having at least one pressure sensor connected thereto;

moving the blood from the upstream T-tube to at least one thrombogenesis unit, the at least one thrombogenesis unit having at least one flow channel;

sucking the blood from the at least one thrombogenesis unit into a downstream T-tube, the downstream T-tube having at least one pressure sensor connected thereto;

activating thrombogenesis within the at least one thrombogenesis unit by using a material within the thrombogenesis unit which promotes thrombogenesis;

maintaining a constant flow through the upstream T-tube, the at least one thrombogenesis unit and the downstream T-tube;

measuring pressure upstream and downstream of the at least one thrombogenesis unit with the sensors while the flow is being maintained constant;

providing a selected fluid flow rate through a diameter of the at least one flow channel to thereby obtain a known shear rate at a wall of the at least one flow channel; and determining over time pressure differences between the upstream and downstream sides of the thrombogenesis unit.

20. The method according to claim 19, further comprising the step of displaying at least one of the volume of the drawn fluid and the pressure differences between the upstream and downstream sides of the thrombogenesis unit.

21. The method according to claim 19, further comprising the step of using a nomogram describing pressure drop per time period for healthy people and for people with circulatory complaints and comparing the determined pressure differences with the nomogram.

* * * * *